United States Patent
Crawford et al.

(10) Patent No.: US 7,416,528 B2
(45) Date of Patent: Aug. 26, 2008

(54) LATCHING DEVICE FOR GASTRIC BAND

(75) Inventors: Norman D. Crawford, Washington Court House, OH (US); Lauren S. Perry, Cincinnati, OH (US); Patrick J. Swindon, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 297 days.

(21) Appl. No.: 11/182,072

(22) Filed: Jul. 15, 2005

(65) Prior Publication Data

US 2007/0015956 A1 Jan. 18, 2007

(51) Int. Cl.
*A61F 2/00* (2006.01)
*B65D 63/00* (2006.01)

(52) U.S. Cl. .................... 600/37; 606/151; 24/16 PB; 24/629

(58) Field of Classification Search ............... 600/37, 600/29–32; 128/897–898; 606/151–158, 606/201–203; 292/307 R; 24/16 PB, 614–615, 24/629
See application file for complete search history.

(56) References Cited

U.S. PATENT DOCUMENTS

| | | | |
|---|---|---|---|
| 4,510,649 A | 4/1985 | Yudis et al. | |
| 4,592,339 A | 6/1986 | Kuzmak et al. | |
| 4,696,288 A | 9/1987 | Kuzmak et al. | |
| 4,760,837 A | 8/1988 | Petit | |
| 5,033,481 A | 7/1991 | Heyler, III | |
| 5,065,772 A | 11/1991 | Cox, Jr. | |
| 5,074,868 A | 12/1991 | Kuzmak et al. | |
| 5,083,576 A | 1/1992 | Ruiz-Razura et al. | |
| 5,160,338 A | 11/1992 | Vincent | |
| 5,226,429 A | 7/1993 | Kuzmak | |
| 5,601,604 A | 2/1997 | Vincent | |
| 5,658,298 A | 8/1997 | Vincent et al. | |
| RE36,176 E | 3/1999 | Kuzmak | |
| 5,910,149 A | 6/1999 | Kuzmak | |
| 6,067,991 A | 5/2000 | Forsell | |
| 6,102,922 A | 8/2000 | Jakobsson et al. | |
| 6,210,347 B1 | 4/2001 | Forsell | |
| 6,450,173 B1 | 9/2002 | Forsell | |
| 6,450,946 B1 | 9/2002 | Forsell | |
| 6,453,907 B1 | 9/2002 | Forsell | |
| 6,454,698 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,460,543 B1 | 10/2002 | Forsell | |

(Continued)

FOREIGN PATENT DOCUMENTS

EP 1319371 6/2003

(Continued)

*Primary Examiner*—John P Lacyk
(74) *Attorney, Agent, or Firm*—Welsh & Flaxman LLC

(57) ABSTRACT

A gastric band includes a band body having a first end and a second end. The band body includes a latching mechanism. The latching mechanism is composed of a shell member at the first end of the band body and a collar member at the second end of the band body, the shell member and collar member being shaped and dimensioned for selective locking and unlocking in a manner creating a loop of the gastric band for positioning about a stomach wall.

32 Claims, 4 Drawing Sheets

U.S. PATENT DOCUMENTS

| | | |
|---|---|---|
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,511,490 B2 | 1/2003 | Robert |
| 6,547,801 B1 | 4/2003 | Dargent |
| 6,676,674 B1 | 1/2004 | Dudai |
| 6,709,385 B2 | 3/2004 | Forsell |
| 6,915,165 B2 | 7/2005 | Forsell |
| 6,916,326 B2 | 7/2005 | Benchetrit |
| 6,953,429 B2 | 10/2005 | Forsell |
| 6,966,875 B1 | 11/2005 | Longobardi |
| 7,011,624 B2 | 3/2006 | Forsell |
| 2003/0019498 A1 | 1/2003 | Forsell |
| 2003/0032857 A1 | 2/2003 | Forsell |
| 2003/0066536 A1 | 4/2003 | Forsell |
| 2003/0092962 A1 | 5/2003 | Forsell |
| 2003/0105385 A1 | 6/2003 | Forsell |
| 2003/0114729 A1 | 6/2003 | Forsell |
| 2004/0049209 A1 | 3/2004 | Benchetrit |
| 2004/0153106 A1 | 8/2004 | Dudai |
| 2004/0158272 A1 | 8/2004 | Hofle et al. |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2005/0002984 A1 | 1/2005 | Byrum et al. |
| 2005/0038458 A1 | 2/2005 | Bailly et al. |
| 2005/0070937 A1 | 3/2005 | Jambor et al. |
| 2005/0119672 A1 | 6/2005 | Benchetrit |
| 2005/0119674 A1 | 6/2005 | Gingras |
| 2005/0183730 A1 | 8/2005 | Byrum et al. |
| 2005/0187566 A1 | 8/2005 | Byrum et al. |
| 2005/0277963 A1 | 12/2005 | Fields |
| 2006/0074439 A1 | 4/2006 | Garner et al. |

FOREIGN PATENT DOCUMENTS

| | | |
|---|---|---|
| EP | 1607072 | 12/2005 |
| EP | 1645249 | 4/2006 |
| WO | WO03/059215 | 7/2003 |
| WO | WO2004/108025 | 12/2004 |
| WO | WO2005/072195 | 8/2005 |
| WO | WO2005/072664 | 8/2005 |

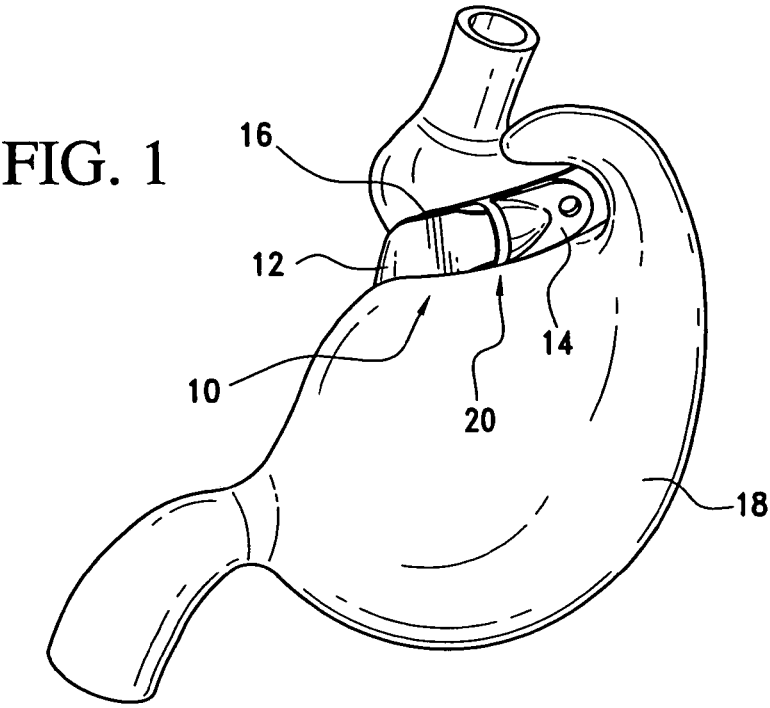
FIG. 1
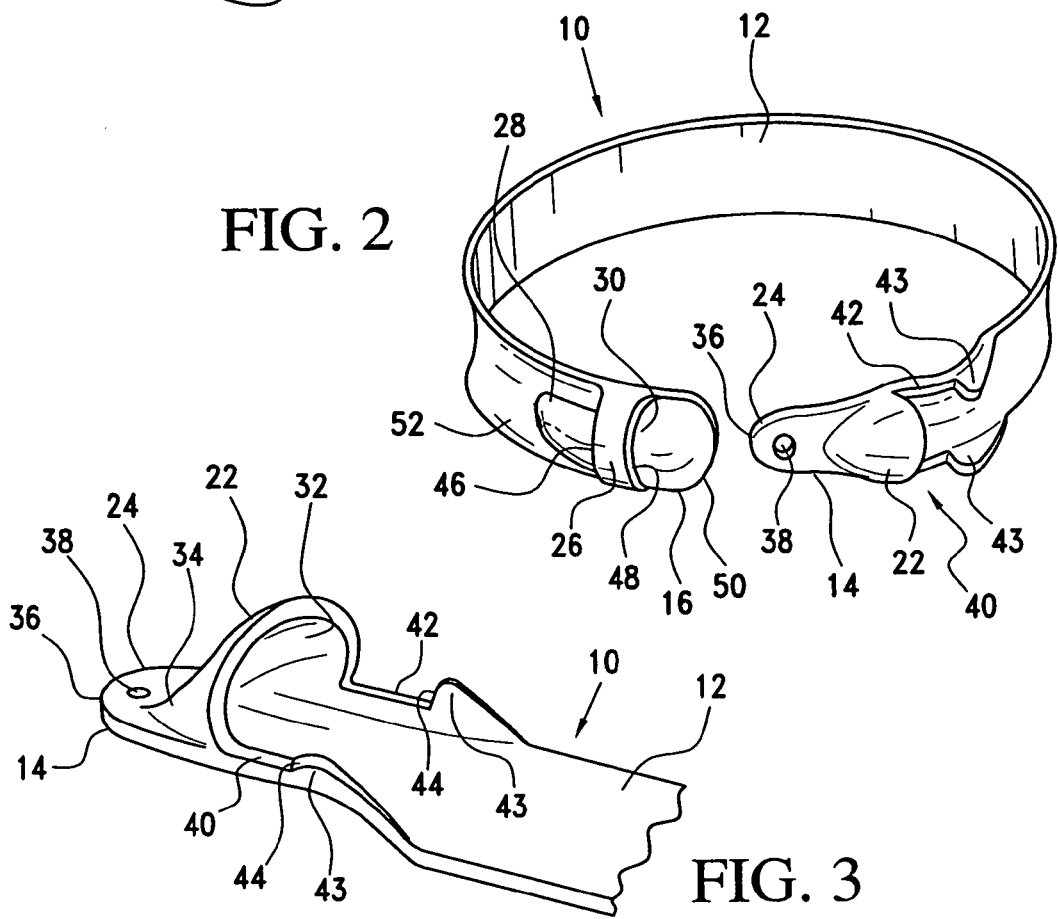
FIG. 2
FIG. 3

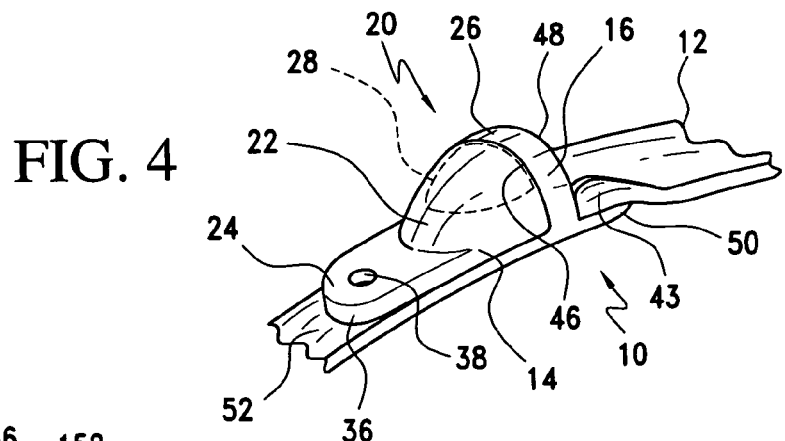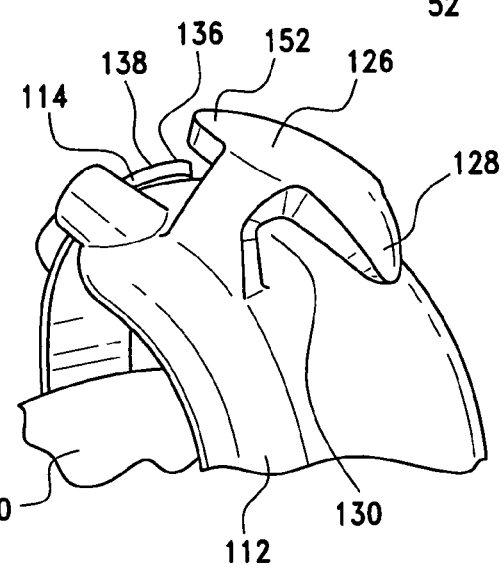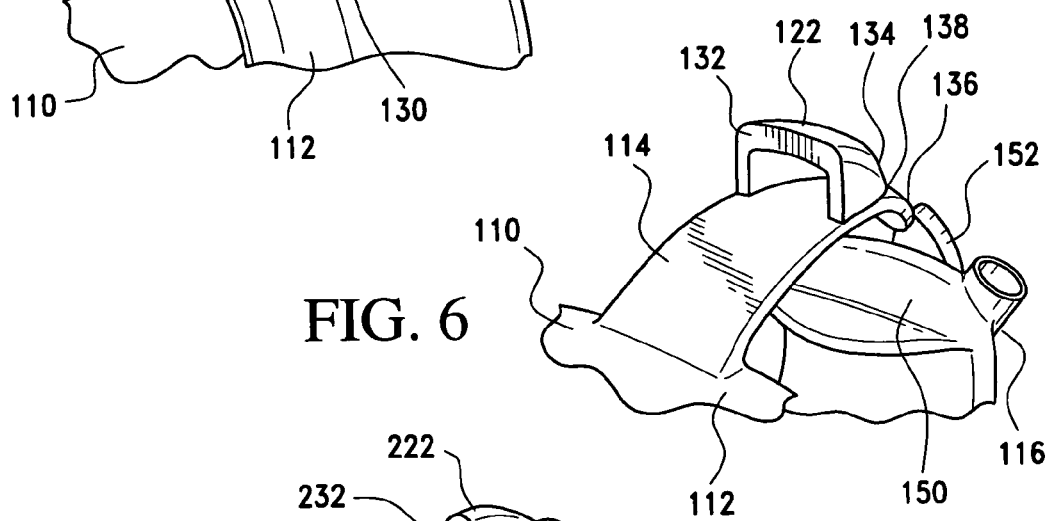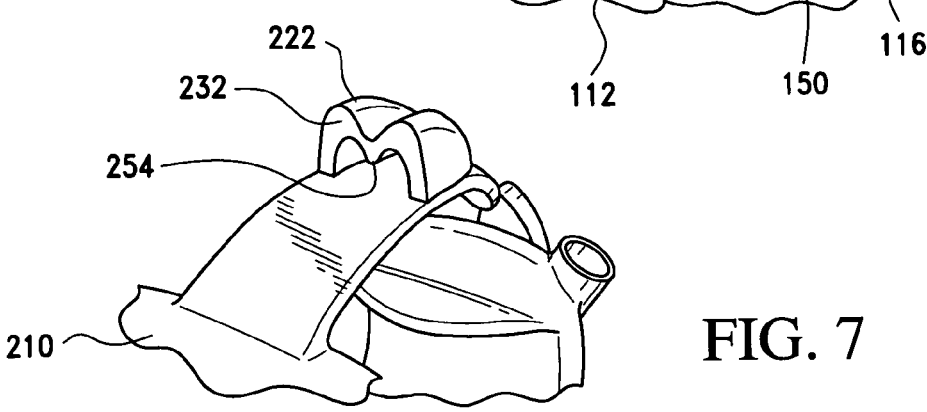

US 7,416,528 B2

LATCHING DEVICE FOR GASTRIC BAND

BACKGROUND OF THE INVENTION

1. Field of the Invention

The invention relates to a gastric band. More particularly, the invention relates to a gastric band with a latching assembly permitting selective locking and unlocking of the gastric band.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980s, gastric bands have provided an effective alternative to gastric bypass and other irreversible surgical weight loss treatments for the morbidly obese. Several alternative procedures are performed under the heading of gastric-banding. Some banding techniques employ a gastric ring, others use a band, some use stomach staples and still other procedures use a combination of rings, bands and staples. Among the procedures most commonly performed are lap band, vertical banded gastroplasty (VBG), silastic ring gastroplasty (SRG), and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages overeating.

Despite the many advantages associated with gastric-banding procedures, it is sometimes desirable to unlatch a previously secured gastric band. However, currently available gastric bands are not easily unlatched and it is often necessary to destroy the gastric band in order to remove and/or adjust the previously applied band. As such, a need currently exists for an improved gastric band which allows for selective locking and unlocking thereof. The present invention provides such a gastric band.

SUMMARY OF THE INVENTION

It is, therefore, an object of the present invention to provide a gastric band with a latching assembly. The gastric band includes a band body having a first end and a second end. The band body includes a latching mechanism composed of a shell member at the first end of the band body and a collar member at the second end of the band body. The shell member and collar member are shaped and dimensioned for selective locking and unlocking in a manner creating a loop of the gastric band for positioning about a stomach wall.

It is also an object of the present invention to provide a gastric band wherein the shell member is generally composed of a hollow, half-moon shaped shell.

It is another object of the present invention to provide a gastric band wherein the shell member further includes a tab for gripping and pulling through the collar member.

It is a further object of the present invention to provide a gastric band including an aperture formed in the tab.

It is also another object of the present invention to provide a gastric band wherein the shell is resilient and compresses when passed through the collar member.

It is still another object of the present invention to provide a gastric band wherein the collar member defines a semi-circular shaped aperture shaped and dimensioned for the passage of the shell member therethrough.

It is also an object of the present invention to provide a gastric band wherein the collar member includes a tongue extending toward a tip of the second end.

It is yet a further object of the present invention to provide a gastric band wherein the shell includes an open, wide end into which the tongue passes after the shell member is passes through the semi-circular shaped aperture.

It is also a further object of the present invention to provide a gastric band wherein the shell member is formed with a substantially M-shaped profile along the wide end thereof.

It is also an object of the present invention to provide a gastric band wherein the tongue is downwardly oriented such that it slides within the wide end of the shell member in a convenient and reliable manner.

It is another object of the present invention to provide a gastric band including a recessed portion formed at the first end of the band body, the recessed portion being shaped and dimensioned for receiving the collar member when the shell member has passed therethrough.

It is a further object of the present invention to provide a gastric band wherein the collar member includes a forward facing gripping member shaped and dimensioned to receive and center the shell member as it passes through the collar member and provide a surface for gripping the collar member.

It is still another object of the present invention to provide a gastric band wherein the tongue is distinctly colored providing a user with an indicator that the latching mechanism is properly fastened.

It is yet another object of the present invention to provide a gastric band wherein the fastening mechanism includes at least one gripping member shaped and dimensioned to permit dual directional access for locking and unlocking of the latching mechanism.

It is a further object of the present invention to provide a gastric band including a band body having a first end and a second end. The band body includes a latching mechanism composed of a first latching member at the first end of the band body and a second latching member at the second end of the band body. The first latching member functions as both a male component and female component during operation of the latching mechanism and the second latching member functions as both a male component and female component during operation of the latching mechanism.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of the present gastric band wrapped about a stomach.

FIG. 2 is a perspective view of a first embodiment in accordance with the present invention.

FIG. 3 is a detailed perspective view of the first end of the gastric band shown in FIG. 2.

FIG. 4 is a perspective view showing the first embodiment latched in accordance with the present invention.

FIGS. 5 and 6 are detailed perspective views of a latching mechanism in accordance with a second embodiment.

FIGS. 7 and 8 are detailed perspective views of a latching mechanism in accordance with a third embodiment.

DESCRIPTION OF THE PREFERRED EMBODIMENTS

Figure 8:
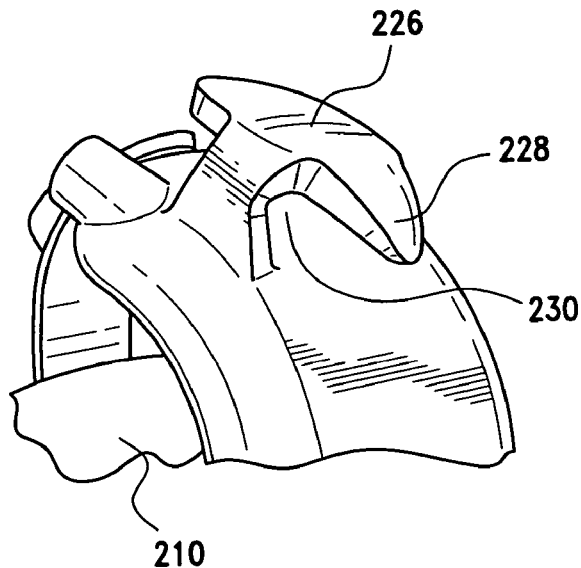
Figure 9:
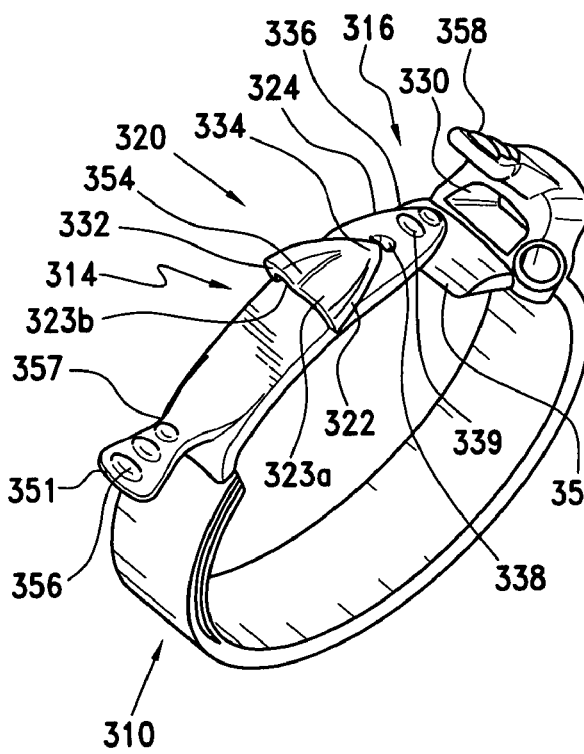
FIGS. 9, 9a, 10 and 11 show a latching mechanism in accordance with a third embodiment of the present invention.
Figure 9A:
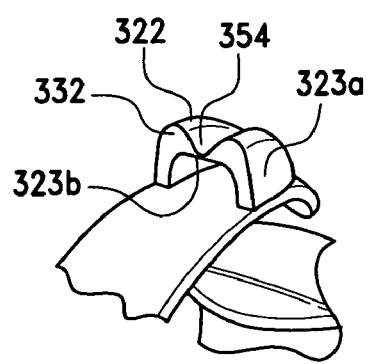
Figure 10:
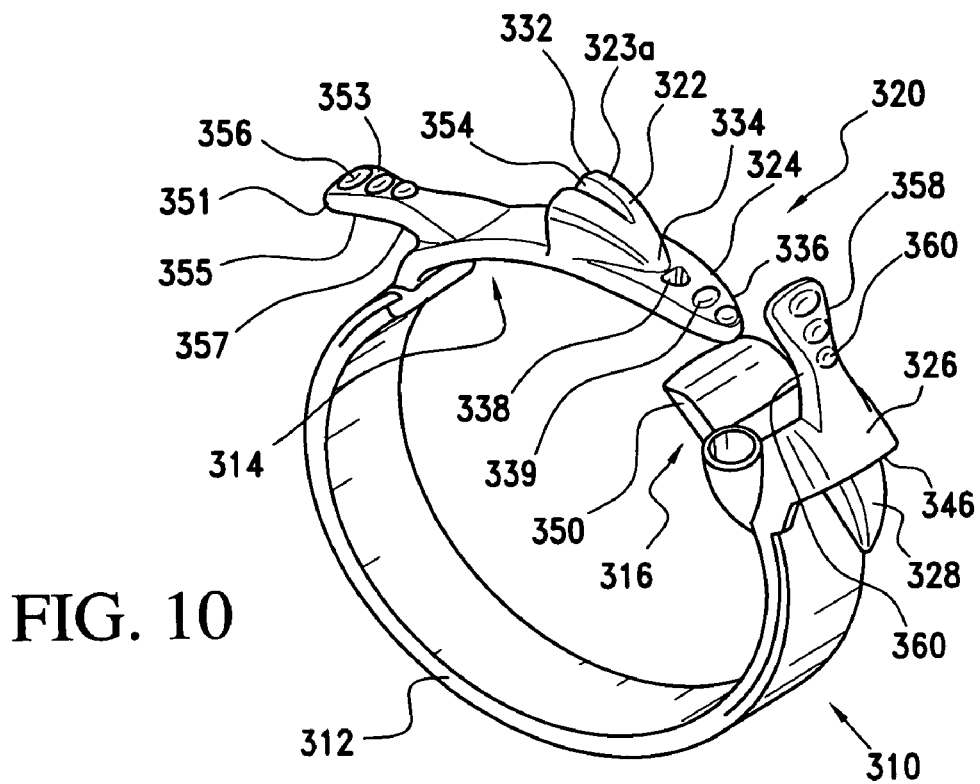
Figure 11:
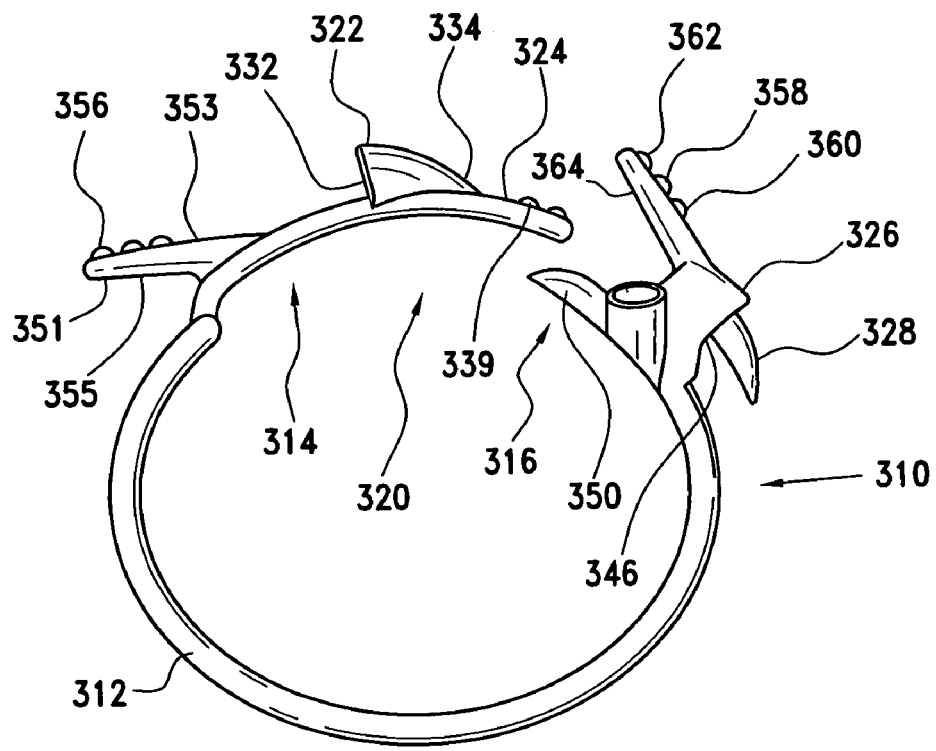

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1, 2, 3 and 4, a first embodiment of a gastric band 10 in accordance with the present invention is disclosed. The gastric band 10 includes a band body 12 having a first end 14 and a second end 16. In accordance with a preferred embodiment, the band body 12 is manufactured from silicone, although other similar materials may be employed without departing from the spirit of the present invention. As those skilled in the art will also certainly appreciate, the present latching mechanism may be used in conjunction with a variety of band structures, including for example, balloon type gastric bands such as those disclosed in commonly owned U.S. Patent Application Publication Nos. 2005/0070937, entitled "SEGMENTED GASTRIC BAND", 2005/0002984, entitled "IMPLANTABLE BAND WITH ATTACHMENT MECHANISM HAVING DISSIMALR MATERIAL PRORPERTIES", 2004/0267291, entitled "IMPLANTABLE BAND WITH NON-MECHANICAL ATTACHMENT MECHANISM", 2004/0267292, entitled "IMPLANTABLE BAND WITH TRANSVERSE ATTACHMENT MECHANISM", 2004/0267288, entitled "IMPLANTABLE BAND HAVING IMPROVED ATTACHMENT MECHANISM", 2004/0267293, entitled "IMPLANTABLE BAND WITH ATTACHMENT MECHANISM", 2004/0254536, entitled "SUBCUTANEOUS SELF ATTACHING INJECTION PORT WITH INTEGRAL FASTENERS", and 2004/0254537, entitled "SUBCUTANEOUS SELF ATTACHING INJECTION PORT WITH INTEGRAL MOVEABLE RETENTION MEMBERS", which are incorporated herein by reference.

Referring to FIG. 1, the gastric band 10 is shaped and dimensioned to circumscribe the stomach 18 at a predetermined location reducing the size of the stomach 18. The gastric band 10 is shown wrapped around an upper portion of a stomach 18 and is kept in place by attaching the first and second ends 14, 16 of the band body 12 together and extending a portion of the stomach 18 over the adjustable gastric band 10 by suturing (not shown) a portion to the stomach 18. The first and second ends 14, 16 of the band body 12 are drawn together to create a loop that is selectively positioned about the stomach wall for reducing the volume thereof in a manner know to those skilled in the art.

Briefly, the present gastric band 10 employs a flexible latching mechanism 20 capable of locking and unlocking without destruction of the latching mechanism 20 or significant reduction in retention capabilities after re-locking. The first and second ends 14, 16 respectively act as both male and female members depending on the direction of motion and intent to lock or unlock the latching mechanism 20 of the present gastric band 10.

Generally, the first end 14 includes a shell member, or first latching member, 22 generally composed of a hollow, half-moon (or semi-circular) shaped shell with a tab 24 for gripping and pulling through a collar member, or second latching member, 26 composed of semi-circular shaped aperture 30 on the second end 16. The half-moon shell of the shell member 22 collapses as it is pulled through the collar member 26 by a grasper.

The collar member 26 includes a tongue 28 such that the shell member 22 slides through the semi-circular shaped aperture 30 and under the tongue 28 during latching. Once the shell member 22 passes the tongue 28, the roles change. The first end 14 functions as a female component when the shell member 22 re-expands to its normally expanded condition and is allowed to slide back onto the second end 16 (now a male component) and over the tongue 28. As such, the shell member 22 functions as both a male component and female component during operation of the latching mechanism 20 and the collar member 26 functions as both a male component and female component during operation of the latching mechanism 20; that is, the shell member 22 functions as a male component during insertion through the collar member 26 and a female component thereafter when the tongue 28 is seated therein.

Unlocking is achieved by employing graspers to squeeze the shell member 22 while pulling the shell member 22 back past the tongue 28 of the collar member 26. While maintaining the shell member 22 squeezed, the shell member 22 is collapsed, becoming a male component, and is slid back under the tongue 28 and through the collar aperture 30 of the second end 16 to unlock. To relock, the same locking procedure is used.

More particularly, and with reference to FIGS. 2, 3 and 4, the shell member 22 at the first end 14 of the gastric band 10 is generally in the shape of a half-moon shaped shell with an open, wide end 32 tapering toward a narrow end 34 adjacent the tip 36 of the first end 14. The shell member 22 is substantially hollow and is formed from a material, for example, silicone, which permits compression and expansion thereof. As those skilled in the art will appreciate, and as shown with regard to the other embodiments disclosed below, the exact shape of the shell member may be varied to suit specific applications and holding requirements.

An aperture 38 is formed within the tab 24 adjacent the tip 36 of the first end 14 and the narrow end 34 of the shell member 22. The aperture 38 is shaped and dimensioned for receipt of a suture, extension member or grasper commonly used in the installation of gastric bands.

Also at the first end 14, but on the opposite side of the shell member 22 from the aperture 38 and adjacent the wide end 32 of the shell member 22, is a recessed portion 40 shaped and dimensioned for receiving the collar member 26 when the shell member 22 has passed therethrough and is in engagement with the tongue 28 of the collar member 26. The recessed portion 40 includes a limited width section 42 with abutments defined by the wide end 32 of the shell member 22 at one end of the recessed portion 40 and tapered abutment members 43 at the other end of the recessed portion 40. The abutment members 43 are tapered to widen as they extend toward the first end 14 of the band body 12 in a manner creating a surface over which the collar member 26 may slide during latching of the first end 14 to the second end 16. The taper also creates opposed abutment surfaces 44 which hold the collar member 26 within the recessed portion 40 when the first end 14 is fully latched to the second end 16.

As to the second end 16 of the band body 12, it generally includes a collar member 26 shaped and dimensioned for the passage of the shell member 22 therethrough in a manner selectively locking the first and second ends 14, 16 together. With this in mind, the collar member 26 generally defines a semi-circular shaped aperture 30 dimensioned for the passage of the shell member 22 therethrough.

Secure fastening of the shell member 22 with the collar member 26 is achieved by ensuring that after the shell member 22 compresses while passing through the collar member 26, the shell member 22 returns to its original shape and the wide end 32 of the shell member 22 abuts with the first edge 46 of the collar member 26. Secure fastening of the shell member 22 with the collar member 26 is further achieved through the provision of the recessed portion 40 in which collar member 26 sits when the first and second ends 14, 16 of the gastric band 10 are latched. When in the recessed portion 40, the first edge 46 of the collar member 26 abuts with the wide end 32 of the shell member 22 and the second edge 48 of the collar member 26 abuts with the abutment surfaces 44 of the abutment members 43.

As mentioned above, latching is further enhanced by providing the collar member 26 with a tongue 28 extending from the collar member 26 away from the tip 50 of the second end 16. The tongue 28 is shaped and dimensioned to seat within the wide end 32 of shell member 22 after the shell member 22 has passed through the collar member 26 and the gastric band 10 is tensioned as the first and second ends 14, 16 are drawn toward each other with the shell member 22 straining to move back through the collar member 26 toward an unlatched positioned. With this in mind, the tongue 28 is downwardly oriented such that it slides within the wide end 32 of the shell member 22 in a convenient and reliable manner.

In accordance with a preferred embodiment of the present invention, the tongue 28 may be colored black, or some other distinguishing color. By coloring the tongue 28 in this way, an indicator is provided as to whether the latching mechanism 20 is properly locked. Particularly, if when the shell member 22 and collar member 26 are secured to together no black of the tongue 28 is showing, the medical practitioner will know the latching mechanism 20 is fully and properly engaged. If a portion of the black tongue 28 is showing, the medical practitioner will know that full engagement has not been achieved and that the shell member 22 and collar member 26 must be relatched.

Guiding of the shell member 22 through the collar member 26 is further facilitated by providing the portion of the second end 16 opposite the tip 50 thereof and the collar member 26 with a recessed guide portion 52 shaped to resemble the bottom of the shell member 22.

As briefly discussed above, the gastric band 10 is latched in the following manner. The gastric band 10 is first positioned at a desired location along the exterior of the stomach 18 and the first end 14 is drawn about the stomach 18 to a position adjacent the second end 16 of the gastric band 10. Thereafter, the first end 14 is drawn through the collar member 26 with the help of a grasper, which engages the tab 24 adjacent the tip 36 of the first end 14. As the shell member 22 at the first end 14 is drawn through the collar member 26, the shell member 22 collapses moving through the collar member 26 and under the tongue 28.

Once the shell member 22 passes the tongue 28, the roles change. The shell member 22 at the first end 14 functions as a female component when the shell member 22 re-expands to its normally expanded condition and is allowed to slide back onto the second end 16 (now a male component) and over the tongue 28 into abutment with the first edge 46 of the collar member 26. At this point, the positioning of the tongue 28 within the shell member 22 and the abutment of the wide end 32 of the shell member 22 with the first edge 46 of the collar member 26 prevent inadvertent unlatching of the first and second ends 14, 16 of the gastric band 10.

The first and second ends 14, 16 are unlatched by employing graspers to squeeze the shell member 22 while pulling the shell member 22 back past the tongue 28 of the collar member 26. While maintaining the shell member 22 squeezed, the shell member 22 is collapsed, becoming a male component, and is slid back under the tongue 28 and through the collar aperture 30 of the second end 16 to unlock. To relock, the same locking procedure is used.

As those skilled in the art will certainly appreciate alternate embodiments are possible without departing from the spirit of the present invention. One such embodiment is disclosed with reference to FIGS. 5 and 6. The shell member 122 at the first end 114 of the gastric band 110 is generally in the shape of a half shell with a wide end 132 tapering toward a narrow end 134 adjacent the tip 136 of the first end 114. The shell member 122 is substantially hollow and is formed from a material which permits compression thereof. A tab 138 is formed adjacent the tip 136 of the first end 114 and the narrow end 134 of the shell member 122. The tab 138 is shaped and dimensioned for grabbing by a grasper.

As to the second end 116 of the band body 112, it generally includes a collar, or buckle, member 126 shaped and dimensioned for the passage of the shell member 122 therethrough in a manner selectively locking the first and second ends 114, 116 together. With this in mind, the collar member 126 generally defines a semi-circular shaped aperture 130 dimensioned for the passage of the shell member 122 therethrough.

Latching is further enhanced by providing the collar member 126 with a tongue 128 extending from the collar member 126 away from the tip 150 of the second end 116. The tongue 128 is shaped and dimensioned to seat within the wide end 132 of the shell member 122 after the shell member 122 has passed through the collar member 126 and the gastric band 110 is tensioned as the first and second ends 114, 116 are drawn toward each other with the shell member 122 straining to move back through the collar member 126 toward an unlatched positioned. With this in mind, the tongue 128 is downwardly oriented such that it slides within the shell member 122 in a convenient and reliable manner. As with the prior embodiment, the tongue 128 may be distinctly colored to provided an indication as to whether the latching mechanism is properly locked.

Guiding of the shell member 122 through the collar member 126 and gripping of the collar member 126 is further facilitated by providing the collar member 126 with a forward facing gripping member 152. The gripping member 152 functions as a tab that may be grasped with a grasper to facilitate locking and unlocking of the gastric band 110. The gripping member 152 is also shaped and dimensioned to receive and center the shell member 122 as it passes through the collar member 126. The gripping member 152 also assists in compressing the shell member 122 as it passes through the collar member. Latching and unlatching of this embodiment is substantially similar to the methodology discussed above.

Another embodiment is disclosed with reference to FIGS. 7 and 8. This embodiment is substantially identical to the embodiment disclosed with reference to FIGS. 5 and 6, however, the shell member 222 is formed with a substantially M-shape when viewed from the wide end 232 thereof. It is contemplated the inclusion of the M-shape in the wide end 232 of the shell member 222 permits ease of unlocking as it will be easier and more controllable for one to compress the shell member.

When this embodiment is employed, the shell member 222 is slid through the collar member 226 as discussed above. Thereafter, the center 254 of the M-shaped wide end 232 is pushed upward to fit over the tongue 228. When the gastric band 210 in accordance with this embodiment is unlatched, the shell member 222 is pulled forward away from the collar member 226 and the M-shaped shell member 222 resiliently returns to its original shape permitting it to move under the tongue 228 and through the collar member 226. As with the prior embodiment, the tongue 228 may be distinctly colored to provided an indication as to whether the latching mechanism is properly locked.

The preformed shape of the shell member 222 not only acts as a guiding feature for the tongue 228 to slide over the shell member 222 during unlocking, but will also allow the shell member 222 to more easily slide back through the aperture 230 of the collar member 226.

Still a further embodiment of the present invention is disclosed with reference to FIGS. 9, 9a, 10 and 11. This embodiment is similar to those described above and includes additional features facilitating greater versatility and improved functionality. The gastric band 310 includes a band body 312 having a first end 314 and a second end 316. As with the prior embodiments, the band body 312 and latching mechanism 320 are preferably manufactured from silicone and the present latching mechanism may be used in conjunction with a variety of band structures, including for example, balloon type gastric bands.

The gastric band 310 is shaped and dimensioned to circumscribe the stomach at a predetermined location reducing the size of the stomach. The gastric band 310 employs a flexible latching mechanism 320 capable of locking and unlocking without destruction of the latching mechanism 320 or significant reduction in retention capabilities after re-locking. The first and second ends 314, 316 respectively act as both male and female members depending on the direction of motion and intent to lock or unlock the latching mechanism 320 of the present gastric band 310.

The first end 314 includes a shell member, or first latching member, 322 generally composed of a hollow, half-moon shaped shell with a tab 324 for gripping and pulling through a collar member, or second latching member, 326 composed of semi-circular shaped aperture 330 on the second end 316. The half-moon shell of the shell member 322 collapses as it is pulled through the collar member 326 by a grasper. The collar member 326 includes a tongue 328 such that the shell member 322 slides through the semi-circular shaped aperture 330 and under the tongue 328 during latching. Once the shell member 322 passes the tongue 328, the roles change. The first end 314 functions as a female component when the shell member 322 resiliently returns to its original shape and is allowed to slide back onto the second end 316 (now a male component) and over the tongue 328. As such, the shell member 322 functions as both a male component and female component during operation of the latching mechanism 320 and the collar member 326 functions as both a male component and female component during operation of the latching mechanism 320; that is, the shell member 322 functions as a male component during insertion through the collar member 326 and a female component thereafter when the tongue 328 is seated therein. Unlocking is achieved by employing graspers to pull the first end 312 forward away from the second end 314 removing the tongue from the shell member. The M-shape of the shell member 322 permits it to collapse and move under the tongue 228 and through the collar member 226.

More particularly, the shell member 322 at the first end 314 of the gastric band 310 is generally in the shape of a half-moon shaped shell with an open, wide end 332 tapering toward a narrow end 334 adjacent the tip 336 of the first end 314. The shell member 322 is substantially hollow and is formed from a material, for example, silicone, which permits compression and expansion thereof.

As briefly mentioned above, and with reference to FIG. 9a, the shell member 322 is formed with a substantially M-shaped outer surface 323a when viewed from the wide end 232 thereof. That is, the outer surface of the shell member 322 has a substantially M-shaped profile, while the inner surface 323b of the shell member 322 adjacent the wide end 332 has a substantially smooth semi-circular profile. The single M-shaped profile has been found to improve flexibility and control as the shell member 322 is passed through the collar member 326. In addition, the inclusion of the M-shape in the wide end 332 of the shell member 322 permits ease of unlocking as it will be easier and more controllable for one to compress the shell member 322.

When this embodiment is employed, the shell member 322 is slid through the collar member 326 as discussed above. Thereafter, the center 354 of the M-shaped wide end 332 returns to its original shape and fits over the tongue 328. When the gastric band 310 in accordance with this embodiment is unlatched, the shell member 322 is pulled forward away from the collar member 326 and the M-shaped shell member 322 permits it to move under the tongue 328 and through the collar member 326. The preformed shape of the shell member 322 not only acts as a guiding feature for the tongue 328 to slide over the shell member 322 during unlocking, but will also allow the shell member 322 to more easily slide back through the aperture 330 of the collar member 326.

An aperture 338 is formed within the tab 324 adjacent the tip 336 of the first end 314 and the narrow end 334 of the shell member 322. The aperture 338 is shaped and dimensioned for receipt of a suture, extension member or grasper commonly used in the installation of gastric bands. In addition, the tab 324 is formed with protrusions 339 assisting in grabbing the tab 324 during locking and unlocking.

Also at the first end 314, but on the opposite side of the shell member 322 from the aperture 338 and adjacent the wide end 332 of the shell member 322, is a rearwardly extending gripping member 351. The gripping member 351 is shaped and dimensioned to permit dual directional access for locking and unlocking of the latching mechanism 320. More particularly, the gripping member 351 includes protrusions 356 along the top and bottom surfaces 353, 355 thereof. These protrusions facilitate gripping thereof along a first directional orientation. The gripping member 350 is further formed with an "hour glass" shaped having a reinforced central section 357. The reinforced central section 357 allows for gripping in a second directional orientation.

As to the second end 316 of the gastric body 312, it generally includes a collar, or buckle, member 326 shaped and dimensioned for the passage of the shell member 322 therethrough in a manner selectively locking the first and second ends 314, 316 together. With this in mind, the collar member 326 generally defines a semi-circular shaped aperture 330 dimensioned for the passage of the shell member 322 therethrough.

Secure fastening of the shell member 322 with the collar member 326 is achieved by ensuring that after the shell member 322 compresses while passing through the collar member 326, the shell member 322 returns to its original shape and the wide end 332 of the shell member 322 abuts with the first edge 346 of the collar member 326.

Latching is further enhanced by providing the collar member 326 with a tongue 328 extending from the collar member 326 away from the tip 350 of the second end 316. The tongue 328 is shaped and dimensioned to seat within the wide end 332 of the shell member 322 after the shell member 322 has passed through the collar member 326 and the gastric band 310 is tensioned as the first and second ends 314, 316 are drawn toward each other with the shell member 322 straining to move back through the collar member 326 toward an unlatched positioned. With this in mind, the tongue 328 may be downwardly oriented such that it slides with the shell member 322 in a convenient and reliable manner. As with the prior embodiment, the tongue 328 may be distinctly colored to provided an indication as to whether the latching mechanism is properly locked.

Gripping of the second end 316 is further enhanced through the provision of a forward facing, that is, facing the tip 350 of the second end 316, gripping member 358. The forward facing gripping member 358 is shaped and dimensioned to permit dual directional access for locking and unlocking of the latching mechanism 320. More particularly, the gripping member 358 includes protrusions 360 along the top and bottom surfaces 362, 364 thereof. These protrusions 360 facilitate gripping thereof along a first directional orientation. The gripping member 358 is further formed with an "hour glass" shape having a reinforced central section 360. The reinforced central section 360 allows for gripping in a second directional orientation.

The gripping member 358 is shaped and dimensioned to receive and center the shell member 322 as it passes through the collar member 326. The guide member 352 also assists in compressing the shell member 322 as it passes through the collar member 326. Latching and unlatching of this embodiment is substantially similar to the methodologies discussed above, and particularly with reference to the embodiment shown in FIGS. 7 and 8.

Although the present invention is described for use in conjunction with gastric bands, those skilled in the art will appreciate the above invention has equally applicability to other types of implantable bands. For example, bands are used for the treatment of fecal incontinence. One such band is described in U.S. Pat. No. 6,461,292. Bands can also be used to treat urinary incontinence. One such band is described in U.S. Patent Application Publication No. 2003/0105385. Bands can also be used to treat heartburn and/or acid reflux. One such band is described in U.S. Pat. No. 6,470,892. Bands can also be used to treat impotence. One such band is described in U.S. Patent Application Publication No. 2003/0114729.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A gastric band with a latching assembly, comprising:
   a band body having a first end and a second end;
   the band body including a latching mechanism, the latching mechanism being composed of a resilient shell member at the first end of the band body and a collar member at the second end of the band body, the shell member and collar member being shaped and dimensioned for selective locking and unlocking in a manner creating a loop of the gastric band for positioning about a stomach wall, wherein shell member compresses and expands upon insertion through the collar member.

2. The gastric band according to claim 1, wherein the shell member is generally composed of a hollow, half-moon shaped shell.

3. The gastric band according to claim 2, wherein the shell member further includes a tab for gripping and pulling through the collar member.

4. The gastric band according to claim 3, further including an aperture formed in the tab.

5. The gastric band according to claim 1, wherein the collar member defines a semi-circular shaped aperture shaped and dimensioned for the passage of the shell member therethrough.

6. The gastric band according to claim 5, wherein the collar member includes a tongue extending toward a tip of the second end.

7. A gastric band with a latching assembly, comprising:
   a band body having a first end and a second end;
   the band body including a latching mechanism, the latching mechanism being composed of a shell member at the first end of the band body and a collar member at the second end of the band body, the shell member and collar member being shaped and dimensioned for selective locking and unlocking in a manner creating a loop of the gastric band for positioning about a stomach wall; and
   wherein the collar member defines a semi-circular shaped aperture shaped and dimensioned for the passage of the shell member therethrough, and the collar member includes a tongue extending toward a tip of the second end, the tongue being distinctly colored providing a user with an indicator that the latching mechanism is properly fastened.

8. The gastric band according to claim 6, wherein the shell member is generally composed of a hollow, half-moon shaped shell.

9. The gastric band according to claim 8, wherein the shell includes an open, wide end into which the tongue passes after the shell member is passes through the semi-circular shaped aperture.

10. The gastric band according to claim 9, wherein the shell member is formed with a substantially M-shaped profile along the wide end thereof.

11. The gastric band according to claim 9, wherein the tongue is downwardly oriented such that it slides within the wide end of the shell member in a convenient and reliable manner.

12. A gastric band with a latching assembly, comprising:
    a band body having a first end and a second end;
    the band body including a latching mechanism, the latching mechanism being composed of a shell member at the first end of the band body and a collar member at the second end of the band body, the shell member and collar member being shaped and dimensioned for selective locking and unlocking in a manner creating a loop of the gastric band for positioning about a stomach wall; and further including a recessed portion formed at the first end of the band body, the recessed portion being shaped and dimensioned for receiving the collar member when the shell member has passed therethrough.

13. The gastric band according to claim 1, wherein the collar member includes a forward facing gripping member shaped and dimensioned to receive and center the shell member as it passes through the collar member and provide a surface for gripping the collar member.

14. The gastric band according to claim 1, wherein the shell member is formed with a substantially M-shaped profile.

15. The gastric band according to claim 1, wherein the fastening mechanism includes at least one gripping member shaped and dimensioned to permit dual directional access for locking and unlocking of the latching mechanism.

16. A gastric band, comprising:
a band body having a first end and a second end;
the band body including a latching mechanism composed of a resilient, first latching member at the first end of the band body and a second latching member at the second end of the band body, the first latching member functions as both a male component and female component during operation of the latching mechanism and the second latching member functions as both a male component and female component during operation of the latching mechanism, wherein the first latching member compresses and expands upon engagement with the second latching member.

17. The gastric band according to claim 16, wherein the first latching member is a shell member and the second latching member is a collar member, the shell member functioning as a male component during insertion through the collar member and a female component thereafter.

18. The gastric band according to claim 17, wherein the shell member is generally composed of a hollow, half-moon shaped shell.

19. The gastric band according to claim 18, wherein the shell member further includes a tab for gripping and pulling through the collar member.

20. The gastric band according to claim 19, further including an aperture formed in the tab.

21. The gastric band according to claim 18, wherein the shell is resilient and compresses when passed through the collar member.

22. The gastric band according to claim 17, wherein the collar member defines a semi-circular shaped aperture shaped and dimensioned for the passage of the shell member therethrough.

23. The gastric band according to claim 22, wherein the collar member includes a tongue extending toward a tip of the second end.

24. A gastric band, comprising:
a band body having a first end and a second end;
the band body including a latching mechanism composed of a first latching member at the first end of the band body and a second latching member at the second end of the band body, the first latching member functions as both a male component and female component during operation of the latching mechanism and the second latching member functions as both a male component and female component during operation of the latching mechanism; and wherein the collar member defines a semi-circular shaped aperture shaped and dimensioned for the passage of the shell member therethrough, and the collar member includes a tongue extending toward a tip of the second end, the tongue being distinctly colored providing a user with an indicator that the latching mechanism is properly fastened.

25. The gastric band according to claim 23, wherein the shell member is generally composed of a hollow, half-moon shaped shell.

26. The gastric band according to claim 25, wherein the shell includes an open, wide end into which the tongue passes after the shell member is passes through the semi-circular shaped aperture.

27. The gastric band according to claim 26, wherein the shell member is formed with a substantially M-shaped profile along the wide end thereof.

28. The gastric band according to claim 26, wherein the tongue is downwardly oriented such that it slides within the wide end of the shell member in a convenient and reliable manner.

29. A gastric band, comprising:
a band body having a first end and a second end;
the band body including a latching mechanism composed of a first latching member at the first end of the band body and a second latching member at the second end of the band body, the first latching member functions as both a male component and female component during operation of the latching mechanism and the second latching member functions as both a male component and female component during operation of the latching mechanism; and further including a recessed portion formed at the first end of the band body, the recessed portion being shaped and dimensioned for receiving the collar member when the shell member has passed therethrough.

30. The gastric band according to claim 17, wherein the collar member includes a forward facing guide member shaped and dimensioned to receive and center the shell member as it passes through the collar member.

31. The gastric band according to claim 17, wherein the shell member is formed with a substantially M-shaped profile.

32. The gastric band according to claim 16, wherein the fastening mechanism includes at least one gripping member shaped and dimensioned to permit dual directional access for locking and unlocking of the latching mechanism.

* * * * *